United States Patent
Schmidt et al.

(10) Patent No.: US 10,336,669 B2
(45) Date of Patent: Jul. 2, 2019

(54) METHOD FOR PREPARING HEXAFLUOROBUTADIENE

(71) Applicant: Arkema France, Colombes (FR)

(72) Inventors: Grégory Schmidt, Saint Andéol le Chateau (FR); Rémy Teissier, Francheville (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/090,851

(22) PCT Filed: Mar. 20, 2017

(86) PCT No.: PCT/FR2017/050635
§ 371 (c)(1),
(2) Date: Oct. 3, 2018

(87) PCT Pub. No.: WO2017/174889
PCT Pub. Date: Oct. 12, 2017

(65) Prior Publication Data
US 2019/0112244 A1 Apr. 18, 2019

(30) Foreign Application Priority Data

Apr. 4, 2016 (FR) ..................... 16 52921

(51) Int. Cl.
| | | |
|---|---|---|
| *C07C 17/21* | (2006.01) | |
| *C07C 17/23* | (2006.01) | |
| *C07C 19/08* | (2006.01) | |
| *C07C 21/20* | (2006.01) | |
| *C07C 17/357* | (2006.01) | |

(52) U.S. Cl.
CPC ............ *C07C 17/357* (2013.01); *C07C 17/21* (2013.01); *C07C 17/23* (2013.01); *C07C 19/08* (2013.01); *C07C 21/20* (2013.01)

(58) Field of Classification Search
CPC ....... C07C 17/357; C07C 17/23; C07C 17/21; C07C 21/20; C07C 19/08
See application file for complete search history.

(56) References Cited

U.S. PATENT DOCUMENTS

| | | |
|---|---|---|
| 2,844,636 A | 7/1958 | Neville et al. |
| 3,287,425 A | 11/1966 | Maynard |

FOREIGN PATENT DOCUMENTS

| | | |
|---|---|---|
| GB | 798407 | 7/1958 |

OTHER PUBLICATIONS

Chambers et al., "Direct syntheses of pentakis(trifluoromethyl)cyclopentadienide salts and related systems", Canadian Journal of Chemistry, 1996, pp. 1925-1929, vol. 74, No. 11.
International Search Report (PCT/ISA/210) dated Jun. 6, 2017, by the European Patent Office as the International Searching Authority for International Application No. PCT/FR2017/050635.
Written Opinion (PCT/ISA/237) dated Jun. 6, 2017, by the European Patent Office as the International Searching Authority for International Application No. PCT/FR2017/050635.

*Primary Examiner* — Jafar F Parsa
(74) *Attorney, Agent, or Firm* — Buchanan Ingersoll & Rooney P.C.

(57) ABSTRACT

The present invention relates to a method for preparing hexafluorobutadiene comprising the following steps: (a) hydrodechlorinating hexachlorobutadiene to form a first stream comprising 1,2,3,4-tetrachlorobutadiene and optionally unreacted hexachlorobutadiene; (b) fluorinating the first stream comprising 1,2,3,4-tetrachlorobutadiene obtained in step (a) to form a second stream comprising 1,1,2,3,4,4-hexafluorobutane, (c) dehydrogenating the second stream comprising 1,1,2,3,4,4-hexafluorobutane to form a third stream comprising hexafluorobutadiene.

13 Claims, No Drawings

METHOD FOR PREPARING HEXAFLUOROBUTADIENE

TECHNICAL FIELD

The invention relates to a process for the preparation of hexafluorobutadiene. In particular, the invention relates to the preparation of hexafluorobutadiene from hexachlorobutadiene.

TECHNOLOGICAL BACKGROUND OF THE INVENTION

Fluorinated compounds have a high potential in numerous fields of application. However, the use of many compounds is limited because of their method of preparation, which is sometimes expensive and/or difficult to implement.

For example, hexafluorobutadiene is used in the etching of electronic components. It is prepared by various processes involving coupling reactions of $C_2$ compounds with fluorine $F_2$. The starting materials are often fluorinated organic compounds containing one or more atoms of another halogen. The preparation of hexafluorobutadiene by coupling of trichloroethylene in the presence of fluorine $F_2$, followed by a series of stages which alternate dehydrochlorination and fluorination by $F_2$, is known in particular from U.S. Pat. No. 8,536,387. This type of reaction tends to generate numerous byproducts which reduces the overall yield of the process.

The preparation of hexafluorobutadiene in four stages: (1) thermal dimerization of 1,2-dichloro-1,2-difluoroethylene to give 1,3,4,4-tetrachloro-1,2,3,4-tetrafluoro-1-butene, (2) chlorination of 1,3,4,4-tetrachloro-1,2,3,4-tetrafluoro-1-butene to give 1,1,2,3,4,4-hexachloro-1,2,3,4-tetrafluorobutane, (3) fluorination of 1,1,2,3,4,4-hexachloro-1,2,3,4-tetrafluorobutane to give 1,2,3,4-tetrachloro-1,1,2,3,4,4-hexafluorobutane, and (4) dechlorination of 1,2,3,4-tetrachloro-1,1,2,3,4,4-hexafluorobutane to give hexafluorobutadiene, is also known from GB 798 407.

Another synthetic route consists in employing reactions for the fluorination of hexachlorobutadiene in the liquid phase. However, these reactions do not make possible the complete fluorination of hexachlorobutadiene to form hexafluorobutadiene. The fluorination of hexachlorobutadiene in the presence of potassium fluoride in order to form a mixture of 2,2-dichloroperfluoropropane and 2-chloro-2-hydroperfluoropropane is known in particular from U.S. Pat. No. 3,287,425.

There thus still exists a need to make possible the preparation of hexafluorobutadiene by selective and affordable reactions.

SUMMARY OF THE INVENTION

According to a first aspect, the present invention provides a process for the preparation of hexafluorobutadiene comprising the stages of:
a) hydrodechlorination of hexachlorobutadiene in order to form a first stream comprising 1,2,3,4-tetrachlorobutadiene and optionally unreacted hexachlorobutadiene,
b) fluorination of said first stream comprising 1,2,3,4-tetrachlorobutadiene obtained in stage a) in order to form a second stream comprising 1,1,2,3,4,4-hexafluorobutane,
c) dehydrogenation of said second stream comprising 1,1,2,3,4,4-hexafluorobutane in order to form a third stream comprising hexafluorobutadiene.

According to a preferred embodiment, the fluorination stage b) can be carried out in the presence of a fluorinating agent of formula $A^{x+}F_x$ in which A is a cation and F denotes a fluoride ion $F^-$.

Preferably, the fluorination stage b) can be carried out in the presence of a fluorinating agent of formula $A^{x+}F_x$ in which A is H, Li, Na, K, Rb, Cs, Mg, Ca, Sr or Ba and x is 1 or 2.

According to a preferred embodiment, the fluorination stage b) can be carried out, in the liquid phase, in the presence of a polar aprotic solvent and of a fluorinating agent of formula $A^{x+}F_x$ in which A is Li, Na, K, Mg or Ca and x is 1 or 2; advantageously, the polar aprotic solvent is chosen from the group consisting of an ether, an amide, an amine, a sulfoxide, a ketone, a nitrile or an ester.

According to a preferred embodiment, the polar aprotic organic solvent can have a boiling point of greater than 100° C. at atmospheric pressure.

According to another preferred embodiment, the fluorination stage b) can be carried out in the gas phase in the presence of a catalyst and of HF.

According to another preferred embodiment, the fluorination stage b) can be carried out in the liquid phase in the presence of HF, advantageously in the presence of a catalyst based on metal halides or on an ionic liquid.

According to a preferred embodiment, hydrochloric acid is also produced during the fluorination stage, said second stream produced in stage b) comprising 1,1,2,3,4,4-hexafluorobutane, hydrochloric acid and optionally the unreacted fluorinating agent; advantageously, the second stream obtained in stage b) is separated into a first flow comprising hydrochloric acid and optionally the unreacted fluorinating agent and into a second flow comprising 1,1,2,3,4,4-hexafluorobutane. In this case, said second flow comprising 1,1,2,3,4,4-hexafluorobutane corresponds to said second stream comprising 1,1,2,3,4,4-hexafluorobutane mentioned in stage c) of the present process.

According to a preferred embodiment, the hexafluorobutadiene formed in stage c) can be recovered and subjected to a distillation stage.

According to a preferred embodiment, stage a) can be carried out in the presence of hydrogen.

According to one embodiment, stage a) can be carried out in the gas phase at a temperature greater than the boiling point of hexachlorobutadiene.

According to a preferred embodiment, stage c) can be carried out by i) chlorination of said second stream comprising 1,1,2,3,4,4-hexafluorobutane and then ii) dechlorination of the product obtained in i) in the presence of a zinc-comprising metal reactant. Preferably, the product obtained in i) is 1,2,3,4-tetrachloroperfluorobutane.

DETAILED DESCRIPTION OF THE INVENTION

According to a first aspect, the invention provides a process for the preparation of hexafluorobutadiene. Said process comprises the successive stages of hydrodechlorination, of fluorination and of dehydrogenation. More particularly, said process comprises the stages of:
a) hydrodechlorination of hexachlorobutadiene in order to form a first stream comprising 1,2,3,4-tetrachlorobutadiene and optionally unreacted hexachlorobutadiene,
b) fluorination of said first stream comprising 1,2,3,4-tetrachlorobutadiene obtained in stage a) in order to form a second stream comprising 1,1,2,3,4,4-hexafluorobutane, c) dehydrogenation of said second stream comprising 1,1,2,3,4,4-hexafluorobutane in order to form a third stream comprising hexafluorobutadiene.

Each stage of the present process can be carried out in one or more reactors arranged in series. The present process can be carried out continuously or batchwise. When a catalyst is used in one of the stages of the process, said catalyst can be regenerated in alternation with the implementation of the stage of the process concerned.

According to a preferred embodiment, the reaction for the hydrodechlorination of hexachlorobutadiene implemented in stage a) is carried out in the presence of hydrogen. Preferably, the hydrogen is introduced in a stoichiometric or superstoichiometric amount.

According to a preferred embodiment, stage a) can be carried out in the gas phase or in the liquid phase. When stage a) is carried out in the gas phase, this can be carried out at a temperature greater than the boiling point of hexachlorobutadiene. In particular, when stage a) is carried out in the gas phase, this can be carried out at a temperature of greater than 220° C., preferably of greater than 250° C., in particular of greater than 270° C. In particular, the temperature at which stage a) is carried out is between 220° C. and 400° C., preferably between 240° C. and 370° C.

Preferably, stage a) of the present process can be carried out in the presence of a supported or unsupported catalyst, said catalyst comprising a transition metal chosen from the metals of Groups 4 to 11 of the Periodic Table. Preferably, said catalyst comprises a transition metal chosen from nickel, cobalt, iron, ruthenium, rhodium, palladium, rhenium, platinum, copper, iridium, osmium, vanadium, chromium, molybdenum, tungsten, zinc or a mixture of these. In particular, said catalyst comprises a transition metal chosen from nickel, cobalt, iron, ruthenium, rhodium, palladium, rhenium, platinum, copper and zinc, or a mixture of these.

Preferably, the catalyst can be supported. The support can be activated carbon or silica or be formed with aluminum, for example alumina, activated alumina or aluminum derivatives, such as aluminum halides and aluminum oxyhalides, for example described in U.S. Pat. No. 4,902,838. Preferably, the support can be activated carbon, alumina, silica or aluminosilicate.

Preferably, the support can have a specific surface of greater than 50 $m^2/g$, advantageously of greater than 75 $m^2/g$, preferably of greater than 100 $m^2/g$, in particular of greater than 125 $m^2/g$ and more particularly of greater than 150 $m^2/g$.

Preferably, the catalyst used in the hydrodechlorination reaction can be in the solid form, preferably in the pellet form. In particular, the catalyst can be deposited on a fixed bed.

According to a specific embodiment, said catalyst used in stage a) of the present process comprises nickel, cobalt, iron, ruthenium, rhodium, palladium, rhenium, platinum, copper or zinc or a mixture of these dispersed over a support with a specific surface of greater than 150 $m^2/g$; in particular, the support is silica, alumina or an aluminosilicate. Preferably, said catalyst used in stage a) of the present process comprises nickel, cobalt, iron, palladium, platinum or copper or a mixture of these dispersed over a support with a specific surface of greater than 150 $m^2/g$; in particular, the support is silica, alumina or an aluminosilicate.

The content by weight of the metal in the catalyst is between 0.01% and 5% by weight, advantageously between 0.05% and 3% by weight, preferably between 0.1% and 2% by weight.

The time of contact between the catalyst and the reactants of stage a) is between 2 s and 60 s, advantageously between 2 s and 45 s, preferably between 5 s and 30 s and in particular between 5 s and 20 s.

Stage a) of the present process can be carried out in the presence of an inert gas, advantageously in the presence of nitrogen, helium or argon, preferably in the presence of nitrogen.

Preferably, the hexachlorobutadiene is vaporized prior to its introduction into the hydrodechlorination reactor. In particular, the hexachlorobutadiene, after vaporization, is mixed with hydrogen and optionally with an inert gas. Preferably, the hexachlorobutadiene, after vaporization, is mixed with hydrogen and nitrogen. This mixing can be carried out before the introduction into the hydrodechlorination reactor or the mixing can be carried out directly in the hydrodechlorination reactor.

Preferably, the hydrogen is introduced with a flow rate of between 0.001 mol/h and 5 mol/h, advantageously between 0.005 mol/h and 0.5 mol/h. Preferably, the hexachlorobutadiene is introduced with a flow rate of between 0.001 mol/h and 5 mol/h, advantageously between 0.005 mol/h and 0.5 mol/h.

According to a preferred embodiment, besides the 1,2,3,4-tetrachlorobutadiene, said first stream obtained in stage a) comprises HCl, unreacted hydrogen and optionally nitrogen.

Advantageously, a stage of separation of the stream of products obtained in stage a) is carried out before stage b).

Preferably, said separation stage comprises the formation of a flow comprising HCl, the unreacted hydrogen and optionally nitrogen and of a second flow comprising 1,2,3,4-tetrachlorobutadiene; in particular, this second flow is used in stage b).

Alternatively, stage a) of the present process can be carried out in the liquid phase. Preferably, stage a) can be carried out in the presence of a solvent. In this embodiment, stage a) of the present process is carried out at a temperature of between 70° C. and 200° C. Advantageously, the solvent used can be a solvent which does not react with hydrogen under the operating conditions of stage a) when the latter is carried out in the liquid phase. Preferably, the solvent can be an ether, an ester or a hydrocarbon.

The hydrocarbon can be an alkane of formula $C_nH_{2n+2}$ in which n is an integer from 5 to 20. The term "ether" refers to a compound of formula $R^1$—O—$R^2$ in which $R^1$ and $R^2$ represent, independently of one another, a $C_1$-$C_{20}$ alkyl, preferably a $C_2$-$C_{15}$ alkyl, in particular a $C_3$-$C_{10}$ alkyl; a $C_6$-$C_{18}$ aryl; a $C_3$-$C_{20}$ cycloalkyl. The term "alkyl" denotes a monovalent radical resulting from a linear or branched alkane comprising from 1 to 20 carbon atoms. The term "cycloalkyl" denotes a monovalent radical resulting from a cycloalkane comprising from 3 to 20 carbon atoms. The term "aryl" denotes a monovalent radical resulting from an arene comprising from 6 to 18 carbon atoms. The term "ester" refers to a compound of formula $R^1$—C(O)—O—$R^2$ in which $R^1$ and $R^2$ represent, independently of one another, a $C_1$-$C_{20}$ alkyl, preferably a $C_2$-$C_{15}$ alkyl, in particular a $C_3$-$C_{10}$ alkyl; a $C_6$-$C_{18}$ aryl; a $C_3$-$C_{20}$ cycloalkyl.

In this alternative embodiment, the hydrogen is introduced in a superstoichiometric amount.

Preferably, the reaction is carried out for a period of time of between 30 minutes and 10 hours, advantageously between 45 minutes and 7 hours, in particular between 1 hour and 4 hours.

Preferably, in this alternative embodiment, stage a) is carried out in an autoclave with stirring. At the end of stage a), the autoclave is decompressed. A nitrogen stream can be introduced into the autoclave before recovery of the reaction mixture. The latter can be concentrated before carrying out stage b) of the present process with this.

Stage b) of the present process is a fluorination reaction which can be carried out in the gas phase or in the liquid phase.

According to a first embodiment, the fluorination stage b) is carried out in the gas phase.

Advantageously, the fluorination stage b) can be carried out in the presence of a fluorinating agent of formula $A^{x+}F_x$ in which A is a cation and F denotes a fluoride ion $F^-$. Preferably, the fluorination stage b) is carried out in the presence of a fluorinating agent of formula $A^{x+}F_x$ in which A is H, Li, Na, K, Rb, Cs, Mg, Ca, Sr or Ba and x is 1 or 2.

The reaction can be carried out in the presence of a supported or unsupported solid catalyst. The catalyst can be a Lewis acid. For example, the catalyst is based on a metal comprising a transition metal oxide or a halide or an oxyhalide of such a metal or the catalyst is a Lewis acid based on a metal comprising aluminum, titanium, niobium, tantalum, tin, antimony, nickel, zinc, hafnium, zirconium or iron.

Preferably, the fluorinating agent is HF. The molar ratio of the hydrofluoric acid to said first stream comprising 1,2,3,4-tetrachlorobutadiene obtained in stage a) is between 1 and 100, preferably between 2 and 70, in particular between 5 and 55.

According to a preferred embodiment, the temperature at which the fluorination stage b) is carried out is between 100° C. and 450° C., advantageously between 125° C. and 400° C., preferably between 150° C. and 380° C.

According to a preferred embodiment, the fluorination stage b) in the gas phase is carried out at a pressure of between 1 and 20 barg, advantageously between 2 and 15 barg, preferably between 3 and 10 barg.

Preferably, stage b) of the present process can be carried out at a temperature of 150° C. to 380° C., at a pressure of 3 to 10 barg, and with a molar ratio of the HF to said first stream comprising 1,2,3,4-tetrachlorobutadiene obtained in stage a) of 5 to 55.

According to a preferred embodiment, hydrochloric acid is also produced during the fluorination stage b). Advantageously, the hydrochloric acid is separated from said second stream comprising 1,1,2,3,4,4-hexafluorobutane; preferably, this separation is carried out prior to stage c), that is to say prior to carrying out the dehydrogenation of said second stream comprising 1,1,2,3,4,4-hexafluorobutane obtained in the fluorination stage b).

According to a specific embodiment, when the fluorinating agent is hydrofluoric acid, said second stream comprises HF, HCl and 1,1,2,3,4,4-hexafluorobutane. Advantageously, the products resulting from stage b) are separated into a first flow comprising HF and HCl and into a second flow comprising the 1,1,2,3,4,4-hexafluorobutane, preferably prior to stage c). Thus, said second flow can be said second stream comprising 1,1,2,3,4,4-hexafluorobutane employed in stage c) of the present process.

According to a second embodiment, the fluorination stage b) can be carried out in the liquid phase.

According to a preferred embodiment, the fluorination stage b) is carried out, in the liquid phase, in the presence of HF. Advantageously, this stage is carried out in the presence of a catalyst based on metal halides or on an ionic liquid.

According to a preferred embodiment, said catalyst can be based on metal halides, in which the metal is chosen from the group consisting of aluminum, titanium, niobium, tantalum, tin, antimony, nickel, zinc, hafnium, zirconium or iron.

According to a preferred embodiment, said catalyst can be an ionic liquid. The ionic liquid can result from a Lewis acid based on a metal chosen from the group consisting of aluminum, titanium, niobium, tantalum, tin, antimony, nickel, zinc, hafnium, zirconium or iron. The ionic liquid is an aqueous salt having an ionic nature and which is liquid at moderate temperatures, preferably at temperatures of less than 120° C.

Preferably, the ionic liquid is obtained by reaction between at least one halide or one oxyhalide of metals chosen from the group consisting of aluminum, titanium, niobium, tantalum, tin, antimony, nickel, zinc, hafnium, zirconium and iron and a salt of general formula $Y^+A^-$ in which $A^-$ represents an anion of halide type or an anion of the antimony hexafluoride type and $Y^+$ represents a cation of quaternary ammonium type, a cation of quaternary phosphonium type or a cation of the tertiary sulfonium type. The term "halide" refers to a chloride, bromide, iodide or fluoride anion or a mixture of these. Mention may more particularly be made of the chlorides, fluorides or chlorides/fluorides of the following formulae:

$TiCl_xF_y$ with x+y=4 and 0≤x<4
$TaCl_xF_y$ with x+y=5 and 0<x≤5
$NbCl_xF_y$ with x+y=5 and 0<x<5
$SnCl_xF_y$ with x+y=4 and 1<x<4
$SbCl_xF_y$ with x+y=5 and 0<x<5

Mention may be made, as examples of such compounds, of the following compounds: $TiCl_4$, $TiF_4$, $TaCl_5$, $TaF_5$, $NbCl_5$, $NbF_5$, $SnCl_4$, $SnF_4$, $SbCl_5$, $SbCl_4F$, $SbCl_3F_2$, $SbCl_2F_3$, $SbClF$, $SbF_5$ and their mixtures. The following compounds are preferably used: $TiCl_4$, $SnCl_4$, $TaCl_5+TaF_5$, $NbCl_5+NbF_5$, $SbCl_5$, $SbFCl_4$, $SbF_2Cl_3$, $SbF_3Cl_2$, $SbF_4Cl$, $SbF$ and $SbCl_5+SbF_5$. The antimony-based compounds are more particularly preferred. Mention may be made, as examples of oxyhalogen-based Lewis acids which can be used according to the invention, of $TiOCl_2$, $TiOF_2$, $SnOCl_2$, $SnOF_2$ and $SbOCl_xF_y$ (x+y=³).

In the $Y^+A^-$ salt, the $Y^+$ cation can correspond to one of the following general formulae: $R^1R^2R^3R^4N^+$, $R^1R^2R^3R^4P^+$ or $R^1R^2R^3S^+$, in which the $R^1$ to $R^4$ substituents, which are identical or different, denote, independently of one another, a saturated or unsaturated, cyclic or noncyclic, or aromatic hydrocarbyl, chlorohydrocarbyl, fluorohydrocarbyl, chlorofluorohydrocarbyl or fluorocarbyl group having from 1 to 10 carbon atoms, it being possible for one or more of these groups to also contain one or more heteroatoms, such as N, P, S or O.

The ammonium, phosphonium or sulfonium cation $Y^+$ can also form part of a saturated or unsaturated or aromatic heterocycle having from 1 to 3 nitrogen, phosphorus or sulfur atoms and can correspond to one or other of the following general formulae:

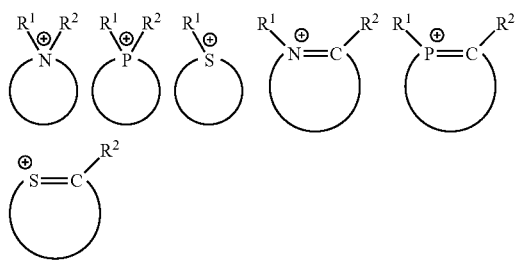

in which R¹ and R² are as defined above.

It would not be departing from the scope of the present invention to use a salt containing 2 or 3 ammonium, phosphonium or sulfonium sites in its formula. Mention may be made, as examples of Y⁺A⁻ salts, of tetraalkylammonium chlorides and fluorides, tetraalkylphosphonium chlorides and fluorides, and trialkylsulfonium chlorides and fluorides, alkylpyridinium chlorides and fluorides, dialkylimidazolium fluorides and bromides, and trialkylimidazolium chlorides and fluorides. Trimethylsulfonium fluoride or chloride, N-ethylpyridinium chloride or fluoride, N-butylpyridinium chloride or fluoride, 1-ethyl-3-methylimidazolium chloride or fluoride, and 1-butyl-3-methylimidazolium chloride or fluoride are more particularly valued.

The ionic liquids according to the invention can be prepared in a way known per se by appropriately mixing the halogenated or oxyhalogen-based Lewis acid and the organic salt $Y^+A^-$ in a molar ratio which can range from 0.5:1 to 3.5:1, preferably from 1:1 to 2.5:1 and more preferably 1:1 to 2:1. A molar ratio strictly of greater than 1:1 is particularly recommended if it is desired to obtain an acidic ionic liquid.

Preferably, the ionic liquid can be based on antimony. For example, the ionic liquid can be the product of the reaction between antimony pentachloride and ethylmethylimidazolium chloride, so as to obtain the catalyst emim $^+Sb_2F_{11}^-$.

The mixing can be carried out in a reactor of autoclave type, optionally cooled in order to limit the exothermicity of the reaction. It is also possible to control this exothermicity by gradually adding one of the reactants to the other.

The molar amount of HF to the molar amount of said first stream comprising 1,2,3,4-tetrachlorobutadiene obtained in stage a) is between 2 and 50 and preferably between 10 and 30. The necessary duration of the reaction, which depends on the amount of the reactants deployed at the start and on the different operating parameters, can be easily known experimentally.

Preferably, the fluorination stage b) in the liquid phase in the presence of HF is carried out at a pressure of 5 to 25 barg.

The material of the fluorination reactor has to make it possible to operate under the pressure and temperature conditions defined above. It also has to withstand the corrosion brought about by the hydrogen fluoride. Thus, stainless steel or alloys of Monel, Inconel or Hastelloy type are particularly indicated.

According to a third embodiment, stage b) of fluorination of said first stream comprising 1,2,3,4-tetrachlorobutadiene obtained in stage a) can be carried out in the presence of a polar aprotic solvent.

Advantageously, the polar aprotic solvent is chosen from the group consisting of an ether, an amide, an amine, a sulfoxide, a ketone, a nitrile and an ester.

Preferably, the polar aprotic organic solvent is chosen from the group consisting of 1,3-dioxane, 1,4-dioxane, 1,3,5-trioxane, tetrahydrofuran, 1,2-dimethoxyethane, dimethyl sulfoxide, diethyl sulfoxide, N-methylpyrrolidone, dimethylformamide, dimethylacetamide, ethyl acetate, acetone, propanone, 2-pentanone, butanone, n-butyl acetate, triethylamine, pyridine and acetonitrile.

In particular, the polar aprotic organic solvent has a boiling point of greater than 100° C. at atmospheric pressure. Preferably, the polar aprotic organic solvent is 1,3-dioxane, 1,4-dioxane, 1,3,5-trioxane, N-methylpyrrolidone, dimethylformamide, dimethylacetamide, propanone, 2-pentanone, butanone, dimethyl sulfoxide or diethyl sulfoxide.

In this third embodiment, the fluorination stage b) is carried out in the presence of a fluorinating agent of formula $A^{x+}F_x$ in which A is a cation and F denotes a fluoride ion $F^-$. Preferably, the fluorination stage b) is carried out in the presence of a fluorinating agent of formula $A^{x+}F_x$ in which A is H, Li, Na, K, Rb, Cs, Mg, Ca, Sr or Ba and x is 1 or 2. In particular, the fluorination stage b) is carried out in the presence of a fluorinating agent of formula $A^{x+}F_x$ in which A is Li, Na, K, Mg or Ca and x is 1 or 2.

Preferably, the molar ratio of the fluorinating agent to said first stream comprising 1,2,3,4-tetrachlorobutadiene is less than 8.7, advantageously less than 8.4, preferably less than 7.8, in particular less than 7.5, more particularly less than 6.9, preferably less than 6.6.

Stage b) can be carried out for a duration of between 1 hour and 10 hours, advantageously from 2 to 6 hours.

Advantageously, stage b) can be carried out at reflux of the solvent.

Preferably, stage b) is carried out, according to this third embodiment, at a pressure of between 0 and 3 barg.

According to a preferred embodiment, the second stream comprising 1,1,2,3,4,4-hexafluorobutane obtained in stage b), according to any one of the embodiments, can be concentrated and/or distilled. For example, the second stream comprising 1,1,2,3,4,4-hexafluorobutane can be distilled at atmospheric pressure between 63° C. and 65° C.

According to stage c) of the present process, said second stream comprising 1,1,2,3,4,4-hexafluorobutane and obtained in stage b) is subjected to a dehydrogenation reaction.

According to a preferred embodiment, stage c) is carried out by i) chlorination of said second stream comprising 1,1,2,3,4,4-hexafluorobutane and then ii) dechlorination of the product obtained in i) in the presence of a metal reactant comprising zinc, copper, manganese or a mixture of these, preferably zinc.

Preferably, stage i) is carried out in the presence of an excess of chlorine. Stage i) can be carried out by a heat treatment, advantageously at a temperature of greater than 80° C., preferably at a temperature of between 120° C. and 150° C. Alternatively, stage i) can be carried out by a photochemical treatment known to a person skilled in the art. Alternatively, stage i) can be carried out in the presence of a radical initiator, such as peroxides or compounds of the azo type, for example azobisisobutyronitrile. In the latter case, stage i) can be carried out at a temperature of between ambient temperature (for example 25° C.) and 80° C.

Preferably, the product obtained in stage i) is a composition comprising 1,2,3,4-tetrachloroperfluorobutane.

Preferably, stage ii) is carried out in the presence of an aqueous and/or alcoholic solvent. For example, stage ii) can be carried out in the presence of water, isopropanol, methanol, ethanol or propanol or a mixture of these. In particular, stage ii) can be carried out in the presence of water, isopropanol or a mixture of these.

Preferably, the third stream comprising the hexafluorobutadiene formed in stage c) is recovered and subjected to a distillation stage.

EXAMPLES

Example 1: Hydrodechlorination of Hexachlorobutadiene

A reactor made of Inox with a length of 500 mm and with an internal diameter of 7.7 mm is charged with a catalyst based on activated carbon impregnated with 8.4% of copper and 1.7% of palladium. The temperature of the catalyst bed is brought to 270° C. A stream of hydrogen and hexachlorobutadiene is then introduced into the reactor. The hexachlorobutadiene and hydrogen flow rates are respectively 0.022 mol/h and 0.086 mol/h. The residence time is 4.8 seconds. The degree of conversion of the hexachlorobutadiene is 78% with a selectivity of 87% for 1,2,3,4-tetrachlorobutadiene. The reaction mixture is recovered by condensation and it is purified by distillation under vacuum (boiling point of 1,2,3,4-tetrachlorobutadiene=188° C.; boiling point of hexachlorobutadiene=210° C.). The 1,2,3,4-tetrachlorobutadiene yield after purification is 60%.

Example 2: Fluorination in the Liquid Phase of 1,2,3,4-tetrachlorobutadiene 100 ml of 1,2,3,4-tetrachlorobutadiene are introduced into 400 ml of HF containing 7 ml of $SbCl_5$ in a 1 1 autoclave maintained at 0° C. The autoclave is equipped with a pressure-regulating valve tared at 20 bar. The stirred mixture is gradually brought to 120° C. The hydrochloric acid produced during the reaction is removed from the autoclave using the regulating valve and then trapped according to methods known to a person skilled in the art. After two hours at 120° C., the reaction mixture is cooled and the excess hydrofluoric acid is removed by distillation. The remaining organic phase is cooled and decanted in order to recover a composition comprising 1,1,2,3,4,4-hexafluorobutane. The composition is distilled and the 1,1,2,3,4,4-hexafluorobutane (boiling point=63-65° C.) is recovered with a yield of 72%.

Example 3: Fluorination in the Gas Phase of 1,2,3,4-tetrachlorobutadiene 5 g of Ni/Cr on $AlF_3$ catalyst are introduced into a tubular reactor with a diameter of 20 mm. The temperature of the catalytic bed is brought to 360° C. and a mixture of 0.28 g/h of 1,2,3,4-tetrachlorobutadiene and of 1.5 g/h of HF (i.e., an HF/1,2,3,4-tetrachlorobutadiene molar ratio of 50) is brought into contact with the catalyst. At the reactor outlet, the unreacted hydrofluoric acid, i.e. 1.3 g/h, and the not completely fluorinated byproducts of the reaction are recycled. A mixture comprising hydrochloric acid and 1,1,2,3,4,4-hexafluorobutane is obtained. The hydrochloric acid and the 1,1,2,3,4,4-hexafluorobutane are separated in order to result in a 1,2,3,4-tetrachlorobutadiene composition of high purity. The 1,1,2,3,4,4-hexafluorobutane yield is 91%, with respect to the 1,2,3,4-tetrachlorobutadiene introduced.

Example 4: Dehydrogenation of 1,1,2,3,4,4-hexafluorobutane 100 g of 1,1,2,3,4,4-hexafluorobutane and 10 g of azobisisobutyronitrile are dissolved in 700 ml of chlorobenzene in a 1-liter stirred glass reactor thermostatically controlled by circulation of a thermal fluid in a jacket, with a pipe for introduction of gas, in this instance chlorine, and connected to a gas trap filled with aqueous sodium hydroxide solution. An amount of chlorine corresponding to approximately 30% of the stoichiometry of the reaction, i.e. 50 g, is introduced at ambient temperature. The stirred mixture is brought to 50° C.; an exotherm of approximately ten degrees appears at about 45° C., which corresponds to the decomposition of the radical initiator, the azobisisobutyronitrile, and to the initiation of the radical chlorination. Chlorine is then introduced at a flow rate of 75 g/h while keeping the temperature of the medium below 60° C. The introduction of chlorine is halted when 150 g of chlorine have been introduced. Reaction is allowed to take place for at least 1 hour after the end of the introduction of the chlorine, until an exotherm is no longer present. The reaction mixture is subsequently flushed with a stream of nitrogen for 30 minutes, then recovered and washed with water. The organic phase is recovered and distilled, in order to obtain a composition comprising 1,2,3,4-tetrachloroperfluorobutane (boiling point=63° C.).

A slightly superstoichiometric amount of metallic zinc, i.e., in this instance, 200 g (1.55 mol of zinc), is introduced into 800 ml of ethanol in a stirred reactor surmounted by a thermostatically controlled reflux condenser connected to a stainless steel cylinder cooled by dry ice. The mixture is stirred, in order to form a suspension of zinc, and the 1,2,3,4-tetrachloroperfluorobutane is introduced at ambient temperature. The reflux condenser is maintained at 0° C. and thus only the hexafluorobutadiene passes through the reflux condenser. 72 g of hexafluorobutadiene are recovered, i.e. a yield of 72% with respect to the 1,1,2,3,4,4-hexafluorobutane. The purity of the hexafluorobutadiene is 98% by GC.

The invention claimed is:

1. A process for the preparation of hexafluorobutadiene comprising the stages of:
   a) hydrodechlorination of hexachlorobutadiene in order to form a first stream comprising 1,2,3,4-tetrachlorobutadiene and optionally unreacted hexachlorobutadiene,
   b) fluorination of said first stream comprising 1,2,3,4-tetrachlorobutadiene obtained in stage a) in order to form a second stream comprising 1,1,2,3,4,4-hexafluorobutane,
   c) dehydrogenation of said second stream comprising 1,1,2,3,4,4-hexafluorobutane in order to form a third stream comprising hexafluorobutadiene.

2. The process as claimed in claim 1, wherein the fluorination stage b) is carried out in the presence of a fluorinating agent of formula Ax+Fx in which A is a cation and F denotes a fluoride ion F—.

3. The process as claimed in claim 2, wherein the fluorination stage b) is carried out in the presence of a fluorinating agent of formula Ax+Fx in which A is H, Li, Na, K, Rb, Cs, Mg, Ca, Sr or Ba and x is 1 or 2.

4. The process as claimed in claim 1, wherein the fluorination stage b) is carried out, in the liquid phase, in the presence of a polar aprotic solvent and of a fluorinating agent of formula Ax+Fx in which A is Li, Na, K, Mg or Ca and x is 1 or 2.

5. The process as claimed in claim 4, wherein the polar aprotic organic solvent has a boiling point of greater than 100° C. at atmospheric pressure.

6. The process as claimed in claim 1, wherein the fluorination stage b) is carried out in the gas phase in the presence of a catalyst and of HF.

7. The process as claimed in claim 1, wherein the fluorination stage b) is carried out in the liquid phase in the presence of HF.

8. The process as claimed in claim 1, wherein hydrochloric acid is also produced during the fluorination stage, said second stream produced in stage b) comprising 1,1,2,3,4,4-hexafluorobutane, hydrochloric acid and optionally the unreacted fluorinating agent.

9. The process as claimed in claim 1, wherein the hexafluorobutadiene formed in stage c) is recovered and subjected to a distillation stage.

10. The process as claimed in claim 1, wherein stage a) is carried out in the presence of hydrogen.

11. The process as claimed in claim 1, wherein stage a) is carried out in the gas phase at a temperature greater than the boiling point of hexachlorobutadiene.

12. The process as claimed in claim 1, wherein stage c) is carried out by i) chlorination of said second stream comprising 1,1,2,3,4,4-hexafluorobutane and then ii) dechlorination of the product obtained in i) in the presence of a zinc-comprising metal reactant.

13. The process as claimed in claim 12, wherein the product obtained in i) is 1,2,3,4-tetrachloroperfluorobutane.

* * * * *